United States Patent
Dallara et al.

(10) Patent No.: US 7,211,098 B2
(45) Date of Patent: May 1, 2007

(54) DILATOR FOR BONE TUNNELS

(75) Inventors: Mark Dallara, Tampa, FL (US); Drew Amery, Clearwater, FL (US)

(73) Assignee: Linvatec Corporation, Largo, FL (US)

(*) Notice: Subject to any disclaimer, the term of this patent is extended or adjusted under 35 U.S.C. 154(b) by 245 days.

(21) Appl. No.: 10/806,188

(22) Filed: Mar. 23, 2004

(65) Prior Publication Data
US 2005/0216013 A1    Sep. 29, 2005

(51) Int. Cl.
*A61F 2/04* (2006.01)
(52) U.S. Cl. .................................... 606/198
(58) Field of Classification Search .............. 606/62, 606/63, 68, 90, 105, 190, 191, 198, 206; 600/215, 218, 220, 222, 224, 225; 604/104–109
See application file for complete search history.

(56) References Cited

U.S. PATENT DOCUMENTS

| | | | | |
|---|---|---|---|---|
| 319,296 A | | 6/1885 | Molesworth | |
| 832,201 A | * | 10/1906 | Kistler | 604/108 |
| 1,331,737 A | * | 2/1920 | Ylisto | 606/198 |
| 5,454,365 A | | 10/1995 | Bonutti | |
| 5,645,547 A | | 7/1997 | Coleman | |
| 5,685,826 A | | 11/1997 | Bonutti | |
| 5,695,515 A | * | 12/1997 | Orejola | 606/191 |
| 5,871,504 A | | 2/1999 | Eaton | |
| 5,888,196 A | | 3/1999 | Bonutti | |
| 6,398,798 B2 | * | 6/2002 | Selmon et al. | 606/159 |
| 6,436,119 B1 | | 8/2002 | Erb et al. | |

* cited by examiner

*Primary Examiner*—Eduardo C. Robert
*Assistant Examiner*—Richard Shaffer
(74) *Attorney, Agent, or Firm*—Michael de Angeli

(57) ABSTRACT

A tool for dilating tunnels in bone, in order to compact the cancellous bone around the tunnel and providing better holding for interference screws and the like, comprises a plurality of elongated segments mounted for radial motion with respect to an axis of elongation. When actuated, the segments move radially outwardly, parallel to the axis of elongation, compacting the bone.

10 Claims, 3 Drawing Sheets

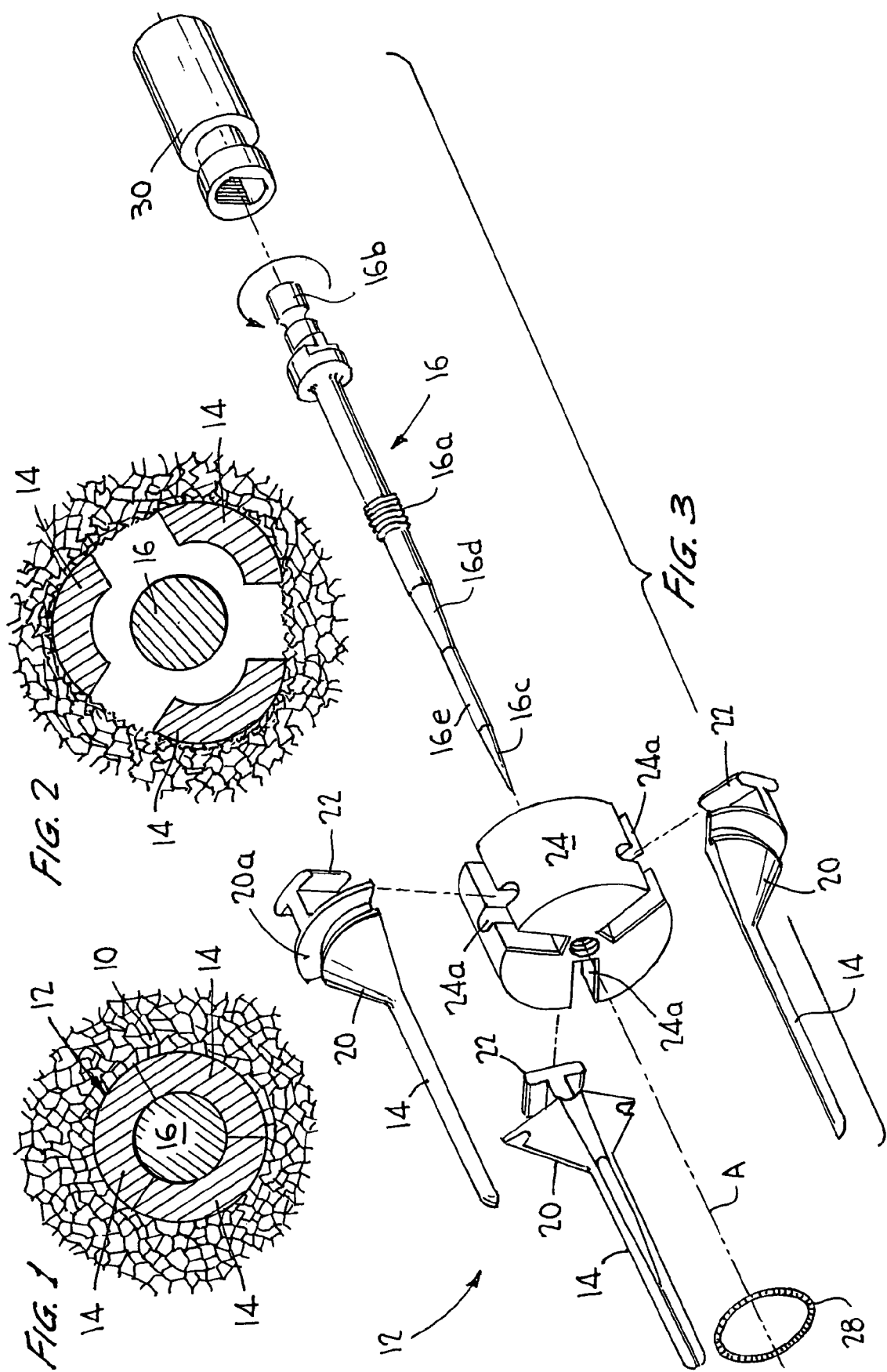

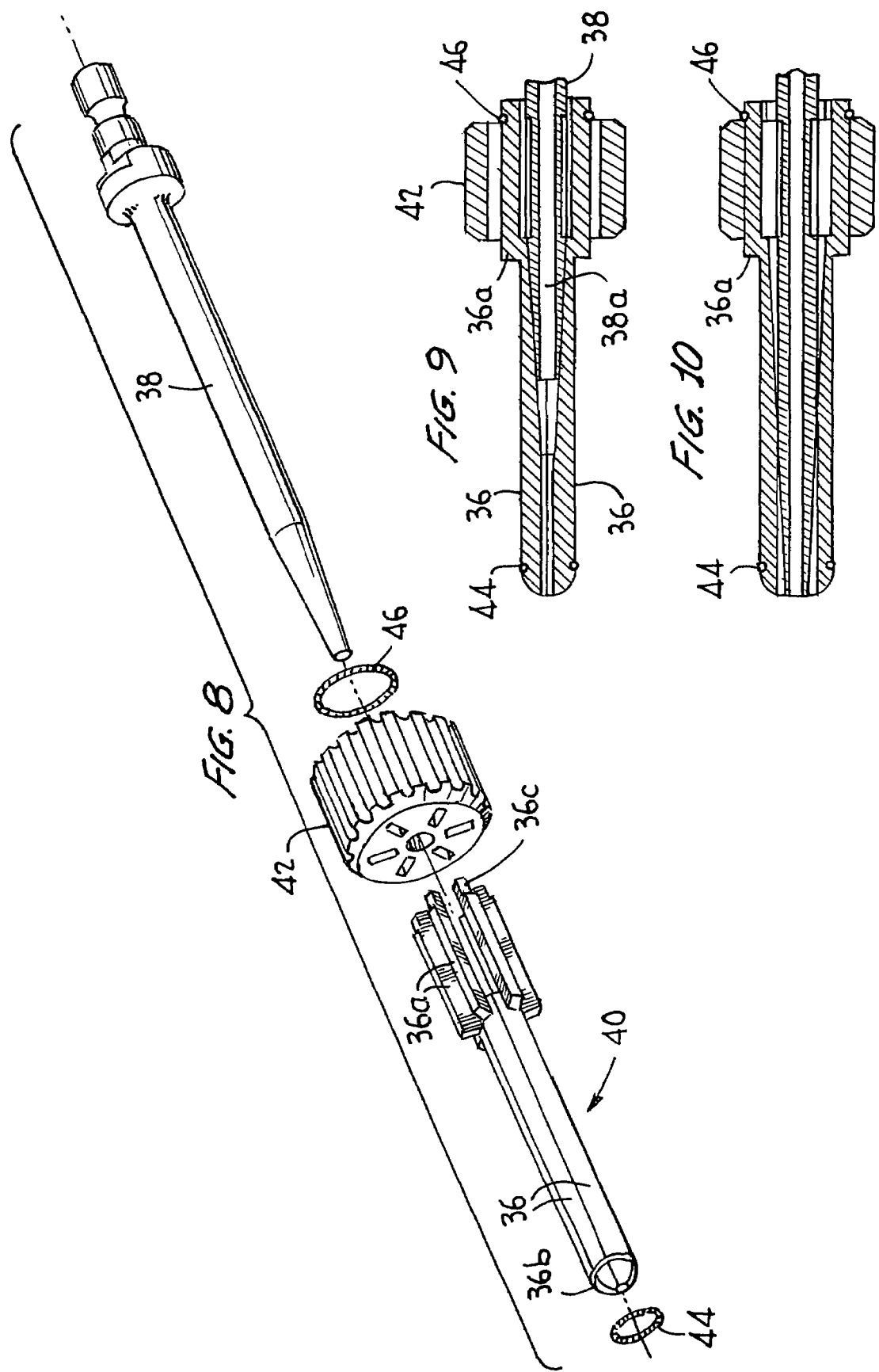

DILATOR FOR BONE TUNNELS

FIELD OF THE INVENTION

This application relates to methods and apparatus for dilation of tunnels bored in bone to receive replacement ligaments and the like, in order to compact and densify the cancellous bone around the tunnel so that it provides a more secure fixation for the component anchoring the ligament to the bone.

BACKGROUND OF THE INVENTION

In various surgical procedures it is desired to anchor a structure in bone; for example, in replacement of damaged anterior cruciate ligaments (ACLs) it is usual to bore tunnels through the opposed bones of the knee joint and anchor a replacement ligament thereto using interference screws. Numerous patents and publications address various aspects of such procedures and provide suggestions to solve various problems connected therewith; see U.S. Pat. Nos. 5,645,547 to Coleman and 5,871,504 to Eaton et al. The Eaton patent in particular illustrates the need for a firm and reliable anchoring technique whereby the ends of a replacement ligament are fixed to the inner walls of tunnels in the bones using threaded fasteners.

As is well known, bones, in particular the long bones such as those of the leg, have a composite structure wherein a hard, dense outer cortex encapsulates a mass of cancellous bone. The tunnels within which replacement ligaments are anchored extend through this cancellous bone, which is relatively soft and spongy, and does not provide good holding for threaded fasteners and the like. In order to improve the holding power of the cancellous bone, it is known to compact the bone surrounding the tunnels, forming a denser structure better adapted to hold threaded fasteners. Typically this has been done by successively driving a series of "torpedo"-shaped members through the tunnels using a hammer; this technique can be used to increase the diameter of a tunnel from 6 mm to 10–12 mm using a series of torpedoes of diameters increasing in 0.5 mm increments. However, this technique is rather crude, involves excessive numbers of steps and of tools, and is generally unsatisfactory.

The art shows several varieties of tools for dilating soft tissues, e.g., for creating space within which to carry out a surgical procedure. See U.S. Pat. Nos. 6,436,119 to Erb et al, and 5,888,196, 5,685,826 and 5,454,365 to Bonutti. Molesworth U.S. Pat. No. 319,296 shows a device described as a combined dilator, drainer, injection and suction syringe. The Molesworth device comprises an outer tubular member which is slit longitudinally from one end so as to form a series of spring prongs defining a segmented outer surface. A tapered inner member can be urged along the lumen of the tubular outer member to force the prongs outwardly, expanding the segments of the outer surface in order to dilate a wound, for example, to enable better irrigation thereof. There is no suggestion in Molesworth that such a device would be of use in compacting cancellous bone in order to better secure an interference screw or the like, and it would seem that friction within the Molesworth device would be excessive in use for such a purpose. Moreover, the Molesworth prongs are not constrained to move outwardly parallel to one another, and so would not be useful in forming a tunnel of regular cylindrical shape in the compacted cancellous bone, as is desired for convenient fixation of anchoring structures.

Accordingly, the art requires a better tool adapted and optimized specifically for dilating and compacting the walls of tunnels formed in cancellous bone to form a tunnel of cylindrical shape.

SUMMARY OF THE INVENTION

According to the present invention, several embodiments of tools for dilating and compacting the walls of tunnels bored in cancellous bone are provided. In each, an elongated member comprises a number of segments arranged about its axis and which can be urged radially outwardly, parallel to the axis of elongation, so that the member is increased in overall diameter. When this tool is disposed in a tunnel in cancellous bone and thus operated, the walls of the tunnel are compacted, forming a larger bore, and providing better holding for a threaded interference screw or other fastener.

In general, the spacing between the segments increases as they move apart, so that a somewhat irregular compacted tunnel is initially formed; preferably, therefore, after a first expansion step the tool is returned to its original configuration, rotated through a partial revolution, and again expanded, so that a regular compacted cylindrical tunnel is formed. In some embodiments the segments are forced outwardly by the interaction of a tapered member urged along a cooperating bore in the tool, and in others the segments may be forced outwardly by a cam rotated within the segmented member.

BRIEF DESCRIPTION OF THE DRAWINGS

The invention will be better understood if reference is made to the accompanying drawings, in which:

FIG. 1 shows a cross-sectional view, taken along line 1—1 of FIG. 4, through a tunnel drilled in cancellous bone, having had the tool of the invention inserted therein, prior to operation of the tool;

FIG. 2 shows a view comparable to FIG. 1, taken along line 2—2 of FIG. 5, after operation of the tool of the invention;

FIG. 3 shows an exploded perspective of a first embodiment of the tool of the invention;

FIG. 8 shows an exploded perspective view of a third embodiment of the tool of the invention;

FIG. 9 shows a partial cross-sectional view through the tool of FIG. 8, prior to operation; and FIG. 10 shows a view comparable to that of FIG. 9, after operation.

DESCRIPTION OF THE PREFERRED EMBODIMENTS

As discussed above, it is an object of the invention to provide an elongated tool for insertion into a tunnel drilled in cancellous bone which can be expanded radially uniformly along its length, so as to compact and densify the surrounding cancellous bone and create a larger-diameter, substantially cylindrical tunnel therein having better properties for holding threaded fasteners and the like. FIGS. 1 and 2 show this schematically: FIG. 1 shows the as-bored tunnel 10 with a tool 12 according to the invention inserted therein, while FIG. 2 shows the result of the tool's having been expanded radially.

Figure 4:
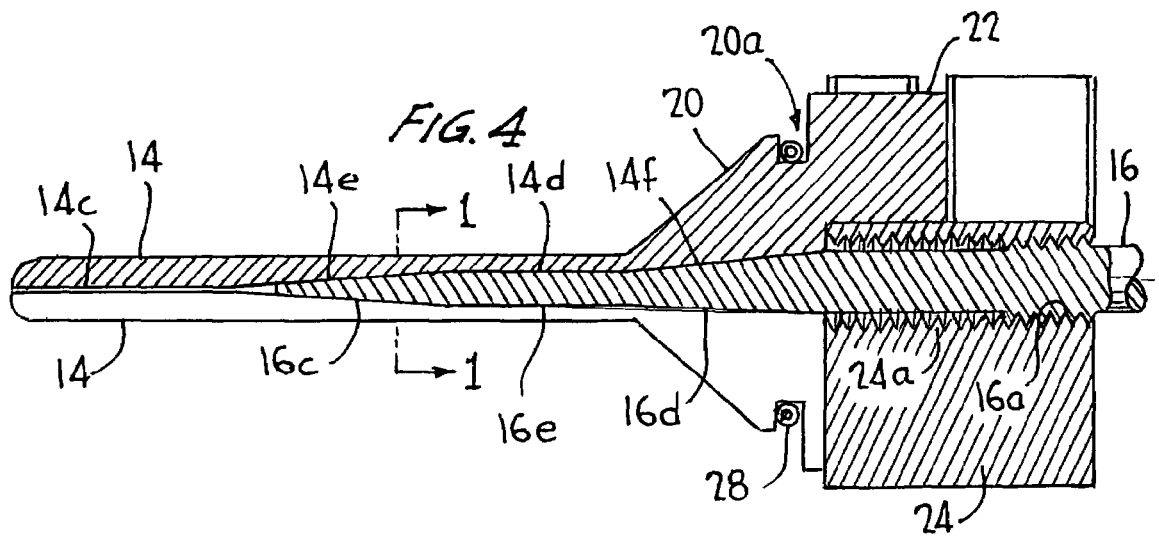
FIG. 4 shows a partial cross-sectional view through the tool in the embodiment of FIG. 3, prior to operation.
Figure 5:
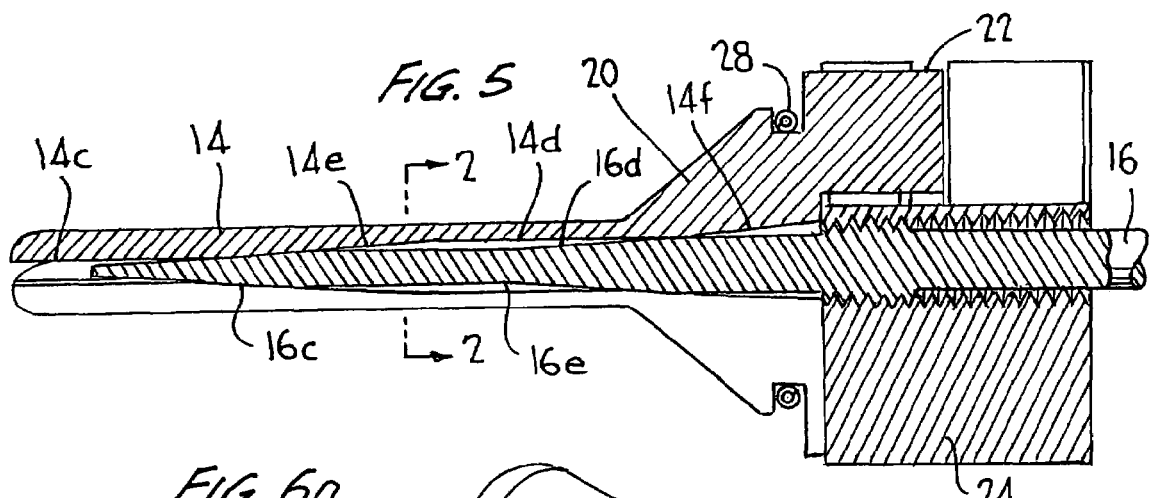
FIG. 5 shows a view similar to FIG. 4, after operation of the tool.

As shown in further detail in FIGS. 3–5, in this embodiment the tool 12 comprises a tapered core member 16 surrounded by three segments 14 meeting at elongated joints. Expansion of the tool as shown in FIG. 2 occurs upon axial motion of the tapered core member 16 with respect to the segments 14, the internal surfaces of which are formed to define a cooperatively-shaped lumen therebetween. As illustrated by FIG. 2, the surrounding cancellous bone has been substantially compacted by the outward movement of the three segments 14 of the tool 12. The bone in the gaps between the segments 14 has not been expanded as completely, but is shown having been pulled outwardly somewhat by its connection with the bone in contact with the three segments of the tool. It is also possible of course to expand the tool 12 at a first position, collapse it again by withdrawal of the core member 16, rotate the entire tool 12 through on the order of 60°, and expand it again, thus forming a more uniformly cylindrical tunnel; the characteristics of the cancellous bone are such that this can be performed equally well after complete expansion of the tool at a first location to a final diameter, or at intervals. Alternatively, a sheath comprising strips of a thin material could be disposed over the joints at which the segments 14 meet, covering the widened spaces therebetween that are formed upon expansion of the tool, and distributing the radial load more uniformly around the circumference of the tool, forming a more closely cylindrical enlarged tunnel.

Although in the embodiments shown the outer surface of the tool forms a cylinder so as to form an enlarged tunnel of uniform circular cross section, as desired for cooperation with the usual threaded members employed to anchor ligaments to bone, it is also within the invention to provide the tool with portions of varying diameter, to form a tunnel of varying diameters, or to shape the tool to form a tunnel of non-circular cross-section, for example, to shape the tool to comprise longitudinal ribs or protrusions to form corresponding shapes in the tunnel.

FIGS. 1–5 show a first embodiment of the tool 12 according to the invention, wherein the tool 12 comprises an elongated cylindrical portion, having an axis A of elongation, and comprising three segments 14, each segment 14 being formed integrally with a hub 20. As illustrated, each hub 20 comprises a "T"-shaped guide 22 which fits within a correspondingly shaped slot 24a extending radially in a knob 24. Thus, the three segments can slide radially inwardly and outwardly with respect to the central axis of the tool 12, so that the outer surfaces of the segments 14 remain parallel to one another. In this way, the enlarged portions of the tunnel formed in the compacted cancellous bone upon operation of the tool are parallel to one another, and, if the tool is collapsed, rotated through on the order of 60°, and operated again, the tunnel thus formed will be essentially cylindrical in cross-section and cooperate well with a threaded fastener. As noted above, this sequence of expansion, collapse, rotation and expansion can be performed several times during the overall process of expanding the tunnel in the cancellous bone to a desired final diameter or once at the final diameter.

The assembly of the three segments is retained over the knob 24, and the segments are urged inwardly, by a garter spring 28 or the like received in grooves 20a extending circumferentially around the hubs 20. In use, the segments are forced outwardly upon operation of the tool by movement of a tapered core member 16 into the assembly of the knob 24 and segments 14, along a cooperating central lumen formed between the inner surfaces of segments 14. See FIGS. 4 and 5. Cooperating threads 16a and 24a are formed on the core member 16 and on the knob 24 respectively, so that the core member 16 is urged into and along the lumen by rotation of the core member 16 with respect to the knob 24.

As illustrated, in the preferred embodiment the core member 16 is formed with two separate conical tapered sections 16c and 16d, connected by a cylindrical portion 16e. The lumen defined by the interior surfaces of the segments 14 similarly comprises two cylindrical portions 14c and 14d separated by an "angled" portion 14e; a further "angled" portion 14f is formed within the hub 20. Portions 14e and 14f of the lumen are "angled" in the sense that they are made up of cylindrical surfaces inclined at an angle to the axis of elongation of the tool, rather than being tapered to match the conical tapered sections 16c and d of the core member 16; the angled cylindrical surfaces are preferred for reasons of reduced friction and wear as compared to mating conical tapered surfaces. Thus, when the core member is initially inserted into the lumen, as illustrated by FIG. 4, the core member fits snugly within the lumen, and, as the core member is urged along the lumen, the tapered portions 16c and 16d of the core member slide along the corresponding angled portions 14c and 14d of the lumen, and the segments are urged outwardly substantially parallel to the axis thereof, as illustrated in FIG. 5.

A similar movement of the segments outward parallel to the axis of elongation of the tool can be achieved by the cooperation of a single longer taper on the core member and a cooperating angled cylindrical surface formed on the lumen (as illustrated in the embodiment of FIGS. 8–10, discussed further below), but there is greater friction in the latter arrangement, and, if the taper is longer, more turns of the threaded member will be needed in order to obtain a given degree of expansion.

In use, therefore, the surgeon inserts the assembly of the segments 14 and knob 24 into the tunnel, inserts the core member 16 into the lumen formed between the segments 14, and turns the core member 16 with one hand while holding the knob 24 with the other, so that threads 16a and 24a cooperate to force the core member 16 along the lumen and urge the segments 14 outwardly, compacting the cancellous bone around the segments. As above, in order to form a regular cylindrical tunnel in the compacted bone, he may choose to expand the tool fully at a first radial position, collapse it, rotate the tool through 60° (in the case of a three-segment tool), and expand it again, to provide a uniformly compacted cylindrical bore in the bone, or the process may be performed iteratively at intermediate degrees of expansion.

A screwdriver-type handle 30 may conveniently be coupled to the proximal end 16b of the core member 16, to provide a gripping surface; the screwdriver handle 30 may be provided with a ratcheting mechanism, so that the surgeon can simply rotate his wrist back and forth to rotate the core member 16 in one direction to advance the core member 16 along the lumen, and need not repeatedly reposition his hand thereon.

In a successfully-tested prototype, the segments 14 with the integral hubs 20 were machined of medical-grade stainless steel, as was the core member 16. The knob 24 was machined of PEEK engineering plastic, to reduce friction as the T-members 22 slide outwardly along the corresponding slots 24a in knob 24. Such a construction is suited for multiple-use tools, which can be reused after sterilization. Of course, other materials and methods of fabrication of the parts may prove desirable. depending on well-understood factors such as sales volumes, the desirability of making disposable tools, and the like. If stainless steel continues to be used for the segments and hub, it might be desirable to make the core member 16 of another material, to reduce friction and galling therebetween, or possibly to coat the core member or the inside surfaces of the segments, or both, with an antifriction coating of suitable type.

Tests performed with tools according to this embodiment of the invention show promise in enlarging bone tunnels from 6 mm diameter to 9 mm in two stages, that is, using two different tools of the design shown; this compares favorably with the hammered "torpedo" tools discussed above, in which the tunnel can only be enlarged in 0.5 mm increments, necessitating six steps to enlarge the tunnel from 6 to 9 mm. The 9 mm tunnel thus formed using the tool of the invention showed good compaction and provided good holding for threaded fasteners and the like.

Figure 6A:
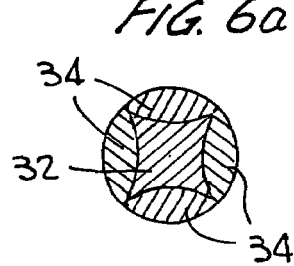
FIG. 6, comprising FIGS. 6(a) and (b), shows respectively a cross-sectional view through and a perspective view of a further embodiment of the tool of the invention, prior to operation.
Figure 6B:
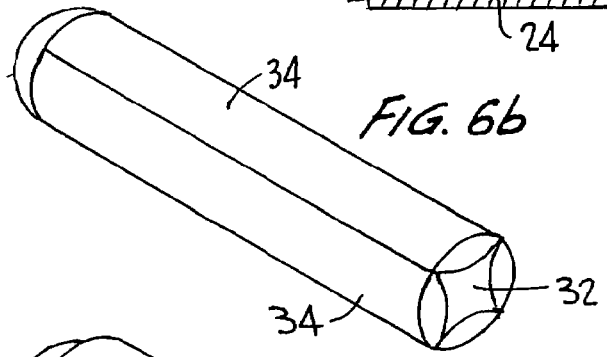
Figure 7A:
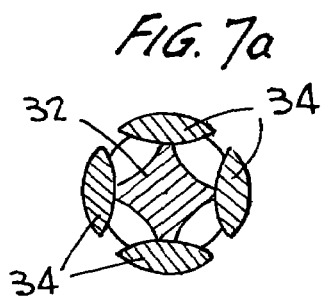
FIG. 7, comprising FIGS. 7(a) and (b), shows views comparable to those of FIG. 6, after operation of the tool.
Figure 7B:
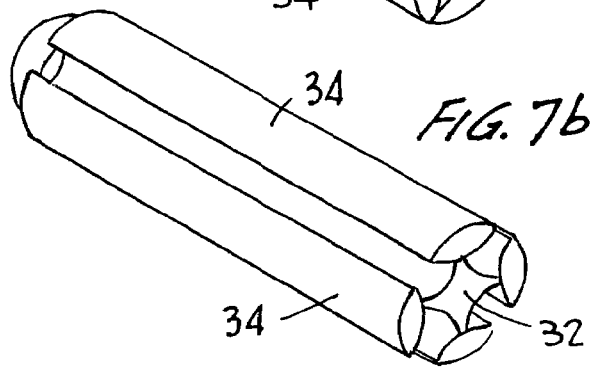

FIGS. 6 and 7 show a partial view of a second embodiment of the tool of the invention. More specifically, FIGS. 6 and 7 show the cylindrical portion of the tool, FIG. 6 in the unexpanded condition in which the tool is inserted in the tunnel to be enlarged so as to compact the surrounding cancellous bone, and FIG. 7 in the expanded state. FIGS. 6(a) and 7(a) show cross-sectional views of the tool and FIGS. 6(b) and 7(b) show perspective views. As illustrated, the cylindrical portion of the tool comprises a central cam member 32, which is surrounded by a number of mating segments 34, four in the example shown. As illustrated, the outer surface of cam 32 is not radially symmetric, while the juxtaposed surfaces of mating segments 34 are cooperatively shaped so that in the unexpanded state of FIG. 6, the segments 34 lie closely against the cam 32. When the cam 32 is rotated through a predetermined angle, which is equal to 360° divided by twice the number of segments, and is thus 45° in the four-segment example shown, the "corners" of the cam, i.e., the portions extending furthest from the central rotational axis of the cam, bear against the surfaces of the segments and force the segments outwardly, as illustrated in FIG. 7.

Not shown in FIGS. 6 and 7, but within the skill of the art, are mechanisms for retaining the segments around the cam and ensuring that they move outwardly uniformly, rather than skew off to one side when the cam is rotated. These aspects of this design can be addressed as in the embodiment of FIGS. 3–5, that is, by employing a garter spring or the like at either or both ends of the assembly to urge the segments inwardly, and providing the segments with hubs having structure cooperating with a knob to permit the segments to move only radially inwardly and outwardly, that is, parallel to the axis of the tool.

It is also within the skill of the art to vary the number of segments 34 in the FIGS. 6 and 7 design (as is also true of the other designs shown) and to vary the shape of the cam. For example, a flat-surface square cam with correspondly-shaped inner surfaces on the mating faces of the segments of a four-segment tool could be substituted for the arc-faced cam shown.

Those of skill in the art will also recognize that the design of FIGS. 6 and 7 will require more torque to operate than that of FIGS. 1–5, since the entire outward expansion takes place over less than 90° revolution of the cam, as opposed to many turns of the threaded core member of the FIGS. 3–5 embodiment; for the same reason, the "corners" of the cam 32 will wear relatively rapidly. For these reasons, the design of FIGS. 1–5 is presently preferred. One advantage of the design of FIGS. 6 and 7 is that the avoidance of a tapered core makes it easier to provide a lumen (not shown) in the cam, so that the tool can be slid over a guide wire into the tunnel; if it were desired to use a guide wire to help locate the tool in the FIGS. 1–5 embodiment, one would typically do so before inserting the tapered core member 16.

FIGS. 8–10 show a further embodiment of the tool of the invention, in which the elongated portion 40 of the tool comprises six segments 36 arranged around a tapered core member 38. FIG. 8 shows an exploded perspective view of the tool, while FIG. 9 shows a cross-section thereof before the core member 38 is inserted, and FIG. 10 shows a corresponding view after insertion of the core member. The segments 36 comprise radially-extending fins 36a, which fit into radial slots in a knob 42, so that the segments are retained in their correct circumferential position, but are permitted to move radially inwardly and outwardly; the T-slotted hub structure of FIGS. 3–5 could also be used, to ensure parallelism of the segments, and other structures for doing so are within the skill of the art. The segments 36 are urged inwardly by garter springs 44 and 46 received in corresponding notches 36b and c, respectively. The segments 36 are forced outwardly by movement of core member 38 into the lumen formed between segments 36; as illustrated, the core member 38 and segments 36 are formed to define corresponding tapered (or tapered and angled, respectively, as above) surfaces, so that the segments 36 are forced outwardly as the core member 38 is forced therealong. The core member 38 and segments 36 might also be formed to define cooperating double tapers, as in the FIGS. 3–5 embodiment, and might also have corresponding threads thereon, so that the core member can be urged along the lumen between the segments by relative rotation thereof, optionally using a ratcheting screwdriver handle as above.

As indicated above, the steps of preparing a bone tunnel for insertion of an anchor for a replacement ligament or the like using the tool of the invention are essentially as follows:

1. A tunnel is prepared in the bone, using a drill, reamer or the like. The diameter of the tunnel must be the same or slightly greater than the diameter of the tool prior to expansion.

2. The elongated portion of the tool is inserted into the tunnel to a desired depth, with the tool in the unexpanded state.

3. The tool is operated in order to cause the segments of the elongated portion to move radially outwardly.

In the embodiment of FIGS. 1–5 (and that of FIGS. 8–10, if similarly provided with cooperating threads) this is performed by rotating the threaded tapered core member a number of times, whereby the cooperating threads on the knob and core member urge the core member along the lumen between the segments, and so that the cooperating tapers formed thereon force the segments outwardly. The rotation can be accomplished manually or by a powered tool.

In the embodiment of FIGS. 6 and 7, the cam is rotated through a partial rotation, equal to 360°/twice the number of segments.

4. The tool is then operated in the opposite manner, to allow the segments to be returned to their original position; in the embodiments shown, the segments are urged toward their original positions by the garter springs stretched over the segments.

5. If desired, the tool can be rotated within the tunnel and operated again, to compact any bone between the segments in the original position.

As above, steps 3–5 can be iteratively performed if it is desired that the tunnel be gradually expanded to a final dimension.

6. If the tunnel is insufficiently dilated by the above steps, the procedure can be repeated using a tool of larger diameter.

While several preferred embodiments of the invention have been disclosed, numerous additional modifications and improvements can be made thereto, and are considered to be within the scope of the invention. Among these are the following:

1. As noted, the tool need not be cylindrical, if some other cross-sectional configuration is desired for the compacted tunnel.

2. Embodiments of tools according to the invention have been shown above having three, four, and six segments making up the elongated portion of the tool that fits within the bone tunnel, and other numbers of segments are of course also possible.

3. A calibrated scale may be provided to allow the degree of dilation to be measured. This could be accomplished, for example, by a scale measuring the degree to which the central member has been inserted into the lumen between the segments, or measuring the degree to which the hubs to which the segments are attached have moved outwardly with respect to the knob.

4. A sheath of thin sheet metal or the like, typically comprising curved members attached to each of the segments and extending over part of the adjoining segment, might be provided over the elongated portion of the tool, covering the gaps that are formed between the segments as they move outwardly, to distribute the radial load more uniformly around the interior of the tunnel, and provide a more uniform interior surface thereto.

5. Various types of cooperative structure on the hubs and the knob might be provided, to ensure that the segments move outwardly essentially parallel to the axis of the tool. For example, the segments could be mounted to the knob by parallelogram-type linkages, and urged outwardly by a threaded member threadedly engaged to the knob and arranged to bear against a proximal joint of each of the linkages.

6. As mentioned above, various materials and methods of fabrication of the parts of the tool are within the skill of the art and the scope of the invention.

Therefore, the above disclosure of the invention should be considered exemplary only and not as limiting thereof; the invention is to be measured only by the following claims.

What is claimed is:

1. A tool for fitting into a tunnel in bone and for being expanded so as to compact the bone surrounding the tunnel, comprising:

a plurality of segments, each comprising an elongated distal portion and a proximal hub portion, a knob for receiving said proximal hub portions of said segments, so that when said segments are assembled to said knob the elongated distal portions of said segments together define an elongated generally cylindrical member extending distally away from said knob on one side thereof, said elongated generally cylindrical member having an axis, and fitting within said tunnel, said knob and said hub portions together defining structure whereby said segments are constrained to move generally inwardly and outwardly with respect to said axis while remaining substantially parallel thereto, such that said elongated generally cylindrical member is increased in diameter as said segments move outwardly with respect to said axis while remaining parallel to one another, and means operable from a position on the opposite side of said knob from said elongated generally cylindrical member for causing said segments to move outwardly with respect to said axis, whereby said bone surrounding said tunnel is compacted permanently by said outwardly-moving segments so that a generally cylindrical bore, larger than said tunnel, is formed in the bone; and wherein each of said segments comprises elongated inner and outer surfaces, and wherein said means operable from a position on the opposite side of said knob from said elongated member comprises a tapered central member fitting within a cooperatively tapered lumen formed about said axis by the inner surfaces of said segments, whereby when said central member is moved distally along said lumen said segments are forced outwardly, while remaining parallel to one another.

2. The tool of claim 1, wherein said central member defines two tapered surfaces joined by a cylindrical section, and said lumen defines two angled cylindrical surfaces joined by a cylindrical section.

3. The tool of claim 2, wherein said lumen comprises a further cylindrical section.

4. The tool of claim 1, wherein said central member and said knob have corresponding threads formed thereon, whereby turning said central member with respect to said knob urges said central member axially along said lumen, whereby said segments are forced outwardly.

5. The tool of claim 1, wherein said structure together defined by said knob and said hub portions, whereby said segments are constrained to move generally inwardly and outwardly with respect to said axis, comprises a radially-extending slot formed in said knob for each segment and a correspondingly-shaped member formed on each hub portion thereof, whereby the segments are constrained to move radially inwardly and outwardly substantially parallel to said axis.

6. The tool of claim 5, wherein said slots in said knob further comprise portions extending transverse to the axis of said elongated member, and said member formed on each hub portion includes a corresponding transverse portion, whereby said segments are further constrained to move parallel to said axis.

7. The tool of claim 1, further comprising means for urging said segments toward said axis, whereby the assembly thereof is maintained.

8. The tool of claim 7, wherein said means for urging said segments toward said axis comprises a garter spring extending around the assembly of said segments at the hub portion thereof.

9. A method for dilating the wall of a tunnel in bone, comprising the steps of:

inserting an elongated section of a tool for dilation into said tunnel, said tool comprising:

a plurality of segments, each comprising an elongated portion and a hub portion, a knob for receiving said hub portions of said segments, so that when said segments are assembled to said knob the elongated portions of said segments together define an elongated member extending away from said knob on one side thereof, having an axis, and fitting within said tunnel, said knob and said hub portions together defining structure whereby said segments are constrained to move generally inwardly and outwardly with respect to said axis, while remaining substantially parallel thereto, and operating means operable from a position on the opposite side of said knob from said elongated member for causing said segments to move outwardly with respect to said axis, said operating means comprising a tapered central member fitting within a cooperatively shaped lumen formed about said axis by the inner surfaces of said segments, said central member and said knob have corresponding threads formed thereon, and engaging said corresponding threads with one another and turning said central member with respect to said knob, urging said central member axially along said lumen, whereby said segments are forced outwardly, and whereby said wall of said tunnel is dilated by said segments.

10. The method of claim 9, comprising the further steps of operating said operating means in an opposite sense, to cause said segments to move inwardly, rotating said tool, and repeating said step of operating said operating means in order to cause said segments to move outwardly with respect to said axis.

* * * * *